United States Patent [19]

Hashimoto et al.

[11] 4,273,623
[45] Jun. 16, 1981

[54] PROCESS FOR RECOVERY OF RESORCIN

[75] Inventors: Isao Hashimoto, Iwakuni; Toru Taguchi, Ichihara; Hirohiko Nambu, Iwakuni, all of Japan

[73] Assignee: Mitsui Petrochemical Industries, Ltd., Tokyo, Japan

[21] Appl. No.: 41,342

[22] Filed: May 22, 1979

[30] Foreign Application Priority Data

May 30, 1978 [JP] Japan ................................. 53/63781

[51] Int. Cl.³ .............................................. B01D 3/34
[52] U.S. Cl. ........................................ 203/92; 203/95; 568/768; 568/810
[58] Field of Search ............... 568/763, 768, 810, 811; 203/95, 96, 91, 92

[56] References Cited

U.S. PATENT DOCUMENTS

| | | | |
|---|---|---|---|
| 2,784,238 | 3/1957 | Jacobs | 568/768 |
| 2,799,715 | 7/1957 | Lohr et al. | 568/768 |
| 3,672,961 | 6/1972 | Nixon | 568/768 |
| 3,923,908 | 12/1975 | Suda et al. | 568/768 |

Primary Examiner—Frank Sever
Attorney, Agent, or Firm—Sherman & Shalloway

[57] ABSTRACT

In the process for obtaining a concentrate of resorcin by acid-decomposing m-diisopropylbenzene hydroperoxide in an inert solvent in the presence of an acidic solid catalyst and distilling off acetone and the inert solvent from the resulting acid-decomposition reaction mixture, if water is added to this reaction mixture in an amount of 20 to 70% by weight based on resorcin and the reaction mixture is then subjected to distillation, resorcin can be obtained at a high recovery yield.

5 Claims, No Drawings

PROCESS FOR RECOVERY OF RESORCIN

BACKGROUND OF THE INVENTION (1) Field of the Invention:

The present invention relates to a process for recovering resorcin at a high recovery yield from an acid-decomposition product of m-diisopropylbenzene dihydroperoxide (hereinafter referred to as "m-DHP").

(2) Description of the Prior Art:

A process for preparing resorcin and acetone by decomposing m-DHP in an inert solvent in the presence of an acid catalyst has been known from old. When an acid type ion exchange resin or an acidic solid catalyst such as silica-alumina is used as the acid catalyst in this process, the resulting reaction mixture need not be neutralized after decomposition reaction and it can be fed to the subsequent step only after separation of the catalyst. Therefore, this process is very advantageous from the industrial viewpoint.

Ordinarily, in order to recover resorcin from the acid-decomposition reaction mixture, acetone and the inert solvent used are removed by distillation. At this distillation step, however, since resorcin has a very high reactivity as is well-known in the art, resorcin is likely to react with carbinols or olefins formed as by-products or with peroxides, and the recovery yield of resorcin is often reduced by these side reactions.

SUMMARY OF THE INVENTION

As a result of our researches made with a view to solving the above problem and developing a process capable of reducing consumption of resorcin at the step of recovering resorcin by distillation of the reaction mixture obtained by acid-decomposition of m-DHP in the presence of an acidic solid catalyst, we found that if a small amount of water is added to this reaction mixture prior to distillation, resorcin can be effectively recovered at a very high recovery yield. Based on this finding, we have now completed the present invention.

More specifically, in accordance with the present invention, there is provided a process for the preparation of resorcin which comprises acid-decomposing m-diisopropylbenzene dihydroperoxide in an inert solvent in the presence of an acidic solid catalyst, separating the catalyst from the acid-decomposition reaction mixture and subjecting the reaction mixture to distillation to separate a resorcin-containing concentrate from acetone formed as a by-product by the acid-decomposition and the inert solvent used for the acid-decomposition, wherein water is added to the acid-decomposition reaction mixture in an amount of 20 to 70% by weight based on resorcin contained in the reaction mixture prior to said distillation and the resulting mixture is then subjected to said distillation.

DETAILED DESCRIPTION OF THE PREFERRED EMBODIMENTS

As is well-known in the art, m-DHP is obtained by liquid-phase air-oxidation of m-diisopropylbenzene and/or m-diisopropylbenzene monohydroperoxide. m-DHP that is subjected to acid-decomposition in the process of the present invention may be either m-DHP separated from the reaction mixture obtained by this oxidation or a residue left after separation of unreacted m-diisopropylbenzene or the like from the oxidation reaction mixture. Furthermore, the oxidation reaction mixture per se may be used as the starting m-DHP in the process of the present invention. Still further, the oxidation reaction mixture may be treated with an oxidant such as hydrogen peroxide to increase the concentration of m-DHP in the oxidation reaction mixture and be then subjected to acid-decomposition in the process of the present invention.

The acid-decomposition reaction is carried out in an inert solvent. As the inert solvent, there may be employed, for example, ketones such as acetone, methylethyl ketone, diethyl ketone and methylisobutyl ketone, and aromatic hydrocarbons such as benzene, toluene, xylene, ethylbenzene, cumene, cymene and diisopropylbenzene. Not only such inert solvent but also various by-products formed by the oxidation, which differ depending on the kind of the starting material subjected to the oxidation, are contained in the starting material to be subjected to the acid-decomposition. In the present invention, it is preferred that m-DHP be contained at a concentration of 15 to 35% by weight in the starting material to be subjected to the acid-decomposition.

In the process of the present invention, an acidic solid catalyst is used for the acid-decomposition reaction. For example, there can be used an ion exchange resin, activated clay, synthetic silica-alumina and synthetic silica-titania. In order to facilitate separation of the acidic solid catalyst from the acid-decomposition reaction mixture, it is preferred that the acidic solid catalyst be used in the form of granules having a size of, for example, 50 to 200 mesh. A preferred amount of the catalyst is 50 to 200% by weight based on m-DHP.

The acid-decomposition reaction is ordinarily carried out at a temperature of 20° to 120° C., preferably 50° to 100° C., under atmospheric or reduced pressure, and reaction conditions such as the reaction temperature and the amount of the catalyst are usually set so that the reaction is completed within 0.5 to 5 hours.

The reaction mixture formed by the acid-decomposition contains not only resorcin, acetone and the inert solvent used but also various by-products, for example, carbinols such as m-isopropyl-$\alpha,\alpha$-dimethylbenzyl alcohol, m-acetyl-$\alpha,\alpha$-dimethylbenzyl alcohol and m-hydroxy-$\alpha,\alpha$-dimethylbenzyl alcohol, olefins such as m-isopropenylphenol, m-isopropenylacetophenone and m-isopropenylcumene, peroxides which are estimated to have been formed by condensation reaction between carbinols or olefins and hydroperoxides, m-isopropylphenol, m-hydroxyacetophenone, and high-boiling-point condensates.

In order to recover resorcin from such acid-decomposition reaction mixture, the acidic solid catalyst is first removed from the reaction mixture, and acetone and the inert solvent are distilled off. Resorcin is likely to react with the above-mentioned carbinols, olefins and peroxides by heating conducted for distillation of acetone and the inert solvent, and in some cases, most of resorcin formed by the acid-decomposition is consumed by such side reaction.

The process of the present invention may be applied to various acid-decomposition reaction mixtures differing in the composition. However, especially good results and high effects can be attained when the process of the present invention is applied to an acid-decomposition reaction mixture containing relatively large amounts of carbinols, olefins and peroxides formed as by-products, for example, an acid-decomposition reaction mixture containing at least 0.1 mole of these by-products per mole of resorcin.

The composition of the acid-decomposition reaction mixture is not particularly critical in the present invention. However, the acid-decomposition reaction mixture ordinarily comprises 0.7 to 1.5 mol/l of resorcin, 6 to 15 mol/l of acetone, 0.5 to 2.5 mol/l of an aromatic hydrocarbon solvent and 0.1 to 0.5 mol/l of at least one member selected from the group consisting of carbinols, olefins and peroxides formed as by-products by acid-decomposition of m-diisopropylbenzene hydroperoxide.

According to the process of the present invention, consumption of resorcin can be effectively prevented at the distillation step only by adding a small amount of water to the acid-decomposition reaction mixture. Water is added to the acid-decomposition reaction mixture, which is a starting material to be subjected to distillation, in an amount of 20 to 70% by weight, preferably 30 to 50% by weight, based on resorcin contained in the reaction mixture. If the amount added of water is smaller than 20% by weight, the effect of inhibiting side reactions is drastically reduced, and even if the amount added of water is increased over 70% by weight, no substantial improvement of the effect of inhibiting side reactions is attained but the heat energy necessary for distillation is increased. Accordingly, too small or too large an amount of water is not preferred. Water is ordinarily added to the acid-decomposition reaction mixture prior to removal of acetone by distillation. Of course, water may be directly supplied to a distillation column for removal of acetone. When a solvent having a boiling point higher than that of acetone is used as the inert solvent and acetone and the inert solvent are distilled off and removed in different distillation columns, it is preferred to adopt a method in which water is added to the reaction mixture prior to removal of acetone by distillation and water is further added to the material to be fed to the distillation column for removal of the inert solvent so that the above-mentioned ratio of water to resorcin is maintained.

In the process of the present invention, distillation is carried out at a temperature of 50° to 180° C., preferably 70° to 140° C. If an inert solvent having a high boiling point is used and this solvent is removed by distillation, it is preferred that distillation be carried out under reduced pressure so that distillation can be performed at a heating temperature included within the above range.

After acetone and the inert solvent have been distilled off according to the process of the present invention, resorcin can be recovered with other by-products by distillation, crystallization, extraction and the like means.

The process of the present invention will now be described in detail by reference to the following Examples and Comparative Examples.

EXAMPLES 1 TO 3 AND COMPARATIVE EXAMPLES 1 AND 2

A reactor having an inner volume of 750 ml and being equipped with an agitator, a thermometer and a cooler was charged with 45 g of commercially available silica-alumina (calcined at 680° C. for 2 hours; silica content=87% by weight; specific surface area=450 m²/g; particle size=75 to 150 mesh) and 129 ml of acetone containing 1.5% by weight of water.

Then, 154 g of toluene solution of an oxidation reaction product obtained by air oxidation of m-diisopropylbenzene and subsequent oxidation with hydrogen peroxide which had the following composition:

| | |
|---|---|
| m-DHP | 43.9% by weight |
| toluene | 27.4% by weight |
| others | 28.7% by weight | to the charge of the reactor under heating and refluxing over a period of 30 minutes, and the acid-decomposition was conducted for one hour at the temperature.

The amount of the residual hydroperoxide in the reaction mixture was analyzed by iodometry and the amount of resorcin was analyzed by gas chromatography. It was found that the conversion of the hydroperoxide was 99.7% and the yield of resorcin was 85%.

The catalyst was removed from the acid-decomposition reaction mixture by stationary separation. The acid-decomposition reaction as mentioned above was repeated to obtain an acid-decomposition reaction mixture ($d_4^{20}$ 0.88) having a composition shown in Table 1.

TABLE 1

| Component | Content (mol/l) |
|---|---|
| Resorcin | 0.927 |
| Carbinols | 0.043 |
| Olefins | 0.024 |
| Peroxides | 0.090 |
| m-Isopropylphenol | 0.094 |
| m-Acetylphenol | 0.051 |
| Acetone | 9.07 |
| Toluene | 1.67 |

A distillation column provided with a 7-staged sieve tray (inner diameter=85 mm, stage spacing=70 mm) was attached to a flask having an inner capacity of 300 ml, and a mixture of the starting mixture shown in Table 1 and a predetermined amount of water was fed at a rate of 1000 ml/hr from the second stage counted from the bottom. Distillation was carried out under conditions of a column top pressure of 150 mmHg, a column bottom heating temperature of 110° C., an average concentrate residence time of 30 minutes in the column bottom and a reflux ratio of 1, and acetone, toluene and water were continuously withdrawn from the column top and the resorcin-containing concentrate was continuously withdrawn from the column bottom. The relation between the amount added of water and the recovery ratio of resorcin was examined to obtain results in Table 2.

TABLE 2

| | Amount Added of Water (% by weight based on resorcin) | Resorcin Recovery Ratio (%) |
|---|---|---|
| Example 1 | 30 | 96.7 |
| Example 2 | 50 | 98.9 |
| Example 3 | 60 | 99.1 |
| Comparative Example 1 | 0 | 84.6 |
| Comparative Example 2 | 15 | 87.5 |

EXAMPLE 4

Acetone was distilled off from the column top under the same conditions as described in Example 2 except that the column top pressure was changed to 760 mmHg and the column bottom heating temperature was changed to 98° C. The concentrate withdrawn from the column bottom (containing resorcin, toluene and water) was collected and was subjected to distillation in the same distillation column under conditions of a column top pressure of 150 mmHg, a column bottom temperature of 110° C., an average concentrate residence time of 15 minutes in the column bottom and a reflux ratio of 1. Thus, toluene and water were distilled off from the column top. The resorcin recovery ratios at distillation of acetone and at distillation of water and toluene were 99.2% and 99.0%, respectively.

COMPARATIVE EXAMPLE 3

Distillation was carried out in the same manner as described in Example 4 except that only the acid-decomposition reaction mixture shown in Table 1 was used as the starting material to be subjected to distillation. The resorcin recovery ratios at distillation of acetone and at distillation of toluene were 92.0% and 91.3%, respectively.

What we claim is:

1. In the process for the preparation of resorcin, by the steps of acid-decomposing m-diisopropylbenzene dihydroperoxide in an inert solvent in the presence of an acid catalyst, separating the catalyst from the acid-decomposition reaction mixture and subjecting the reaction mixture to distillation to separate a resorcin-containing concentrate from acetone formed as a by-product and the inert solvent, the improvement comprising carrying out the acid-decomposition of the dihydroperoxide in the presence of an acidic solid catalyst in an amount of 50 to 200% by weight based on the dihydroperoxide, adding water to the acid decomposition reaction mixture in an amount of 20 to 70% by weight based on resorcin contained in the reaction mixture prior to the distillation and subjecting the resulting mixture to said distillation.

2. A process for the preparation of resorcin according to claim 1 wherein the acid-decomposition reaction mixture to which water has been added is subjected to distillation at a temperature of 70° to 140° C. under atmospheric or reduced pressure.

3. A process for the preparation of resorcin according to claim 1 wherein said acid-decomposition reaction mixture containing at least one member selected from the group consisting of carbinols, olefins and peroxide formed as by-products by said acid-decomposition in an amount of at least 0.1 mole per mole of resorcin contained in said reaction mixture.

4. A process for the preparation of resorcin according to claim 1 wherein water is added to said acid-decomposition reaction mixture in an amount of 30 to 50% by weight based on resorcin contained in said reaction mixture.

5. A process for the preparation of resorcin according to claim 1 wherein said acid-decomposition reaction mixture is a mixture comprising 0.7 to 1.5 mol/l of resorcin, 6 to 15 mol/l of acetone, 0.5 to 2.5 mol/l of an aromatic hydrocarbon solvent and 0.1 to 0.5 mol/l of at least one member selected from the group consisting of carbinols, olefins and peroxides, which have been formed as by-products by said acid-decomposition reaction of m-diisopropylbenzene dihydroperoxide.

* * * * *